United States Patent
Mukaibatake

(10) Patent No.: US 9,218,948 B2
(45) Date of Patent: Dec. 22, 2015

(54) MASS SPECTROMETER

(75) Inventor: Kazuo Mukaibatake, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/386,453

(22) PCT Filed: Mar. 22, 2012

(86) PCT No.: PCT/JP2012/057272
§ 371 (c)(1),
(2), (4) Date: Sep. 19, 2014

(87) PCT Pub. No.: WO2013/140558
PCT Pub. Date: Sep. 26, 2013

(65) Prior Publication Data
US 2015/0108348 A1    Apr. 23, 2015

(51) Int. Cl.
*H01J 49/14* (2006.01)
*G01N 27/00* (2006.01)
(Continued)

(52) U.S. Cl.
CPC ............ *H01J 49/06* (2013.01); *G01N 27/62* (2013.01); *H01J 49/062* (2013.01); *H01J 49/10* (2013.01)

(58) Field of Classification Search
CPC ............ H01J 49/424; H01J 49/004063; H01J 49/423; H01J 49/005; H01J 49/0031; H01J 49/0081; H01J 49/025; H01J 49/14; H01J 49/4225; H01J 49/4265; H01J 49/427; H01J 49/429; G01N 27/624; G01N 27/622; G01N 30/7266
USPC ......... 250/282, 281, 292, 290, 283, 287, 288, 250/286, 291, 293
See application file for complete search history.

(56) References Cited

U.S. PATENT DOCUMENTS 5,120,957 A * 6/1992 Griffiths .................. 250/282
5,463,219 A * 10/1995 Buckley et al. ........... 250/281
(Continued)

FOREIGN PATENT DOCUMENTS

JP    2009-192388 A    8/2009

OTHER PUBLICATIONS

John P. Guzowski et al., "Characteristics of a rf-only hexapole ion-guide interface for plasma-source time-of-flight mass spectrometry", Journal Analytical Atomic Spectrometry., Aug. 2001, pp. 781-792, vol. 16, No. 8.

(Continued)

*Primary Examiner* — David A Vanore
(74) *Attorney, Agent, or Firm* — Sughrue Mion, PLLC

(57) ABSTRACT

The larger an m/z to be adjusted, the wider a peak width which represents change in intensity in relation to change in voltage. This allows voltage step size to be increased during a search for an optimum voltage without overlooking a maximum intensity. Thus, a relational expression which gives a narrow voltage step size for a low m/z and gives a wide voltage step size for a high m/z is prestored in a voltage step information storage unit (32), an optimum voltage adjustment controller (31) finds an optimum voltage step size for the m/z to be adjusted, during automatic voltage adjustment using the stored information, and controls a power supply unit 21 so as to change a voltage applied to a first ion guide (8) stepwise. Ion intensity obtained each time the applied voltage changes is determined, and a voltage value which gives a maximum ion intensity is found and stored in an optimum voltage information storage unit (33). Consequently, during automatic adjustment of a voltage applied to an ion transport optical element such as an ion guide, the time required for the adjustment can be reduced without overlooking an optimum voltage value which gives a maximum ion intensity.

4 Claims, 4 Drawing Sheets

(51) Int. Cl.
*H01J 49/06* (2006.01)
*G01N 27/62* (2006.01)
*H01J 49/10* (2006.01)

(56) References Cited

U.S. PATENT DOCUMENTS

| | | | | |
|---|---|---|---|---|
| 5,468,957 | A * | 11/1995 | Franzen | 250/282 |
| 6,621,077 | B1 * | 9/2003 | Guevremont et al. | 250/292 |
| 7,157,698 | B2 * | 1/2007 | Makarov et al. | 250/281 |
| 7,342,224 | B2 * | 3/2008 | Makarov et al. | 250/290 |
| 7,507,953 | B2 * | 3/2009 | Makarov et al. | 250/287 |
| 2004/0149903 | A1 * | 8/2004 | Wang | 250/292 |
| 2005/0109931 | A1 * | 5/2005 | Schultz et al. | 250/287 |
| 2008/0054173 | A1 * | 3/2008 | Yasuda et al. | 250/283 |
| 2008/0149824 | A1 * | 6/2008 | Miller et al. | 250/287 |
| 2009/0212209 | A1 * | 8/2009 | Quarmby | 250/283 |
| 2013/0105682 | A1 * | 5/2013 | Geromanos et al. | 250/282 |

OTHER PUBLICATIONS

International Search Report for PCT/JP2012/057272 dated Jun. 12, 2012.
Extended European Search Report issued Apr. 15, 2015 in European Patent Application No. 12872192.5.

* cited by examiner m/z=M1 m/z=M2 (>M1)

MASS SPECTROMETER

CROSS REFERENCE TO RELATED APPLICATIONS

This application is a National Stage of International Application No. PCT/JP2012/057272 filed Mar. 22, 2012, the contents of which are incorporated herein by reference in their entirety.

TECHNICAL FIELD

The present invention relates to a mass spectrometer, and more particularly, to a technique for automatically adjusting a voltage or voltages applied to an ion transport optical system provided to transport ions to a subsequent stage in the mass spectrometer.

BACKGROUND ART

Normally, the mass spectrometer uses plural ion transport optical elements to transport ions to a subsequent stage while suppressing dispersion of ions originating from sample. In a liquid chromatograph mass spectrometer (LC/MS) described in Patent Literature 1, for example, a desolvation pipe, an ion guide known as a Q array, a skimmer, an octupole ion guide, an entrance lens electrode, a pre-rod electrode, and the like disposed between an ion source and a quadrupole mass filter which is a mass spectrograph are all ion transport optical elements.

In a tandem quadrupole mass spectrometer (also known as a triple-quadrupole mass spectrometer), ions are fragmented by collision induced dissociation (CID) in a collision cell, and the generation efficiency of a targeted product ion by the fragmentation depends on the energy (collision energy) of an ion entering the collision cell. The collision energy depends on the voltages applied to the collision cell and the ion transport optical element in a preceding stage, and the ion intensity changes when the voltages are changed. Thus, it can be said that the collision cell is also an ion transport optical element in a broad sense.

The optimum voltage values of the ion transport optical elements that give maximum ion intensity slightly vary from spectrometer to spectrometer. Further, the optimum voltage values vary depending on the mass-to-charge ratio of a component to be analyzed. Therefore, in order to perform a high-sensitivity and high-accuracy analysis, an operation in search of the optimum voltage value to be applied to each ion transport optical element needs to be carried out at each mass-to-charge ratio on a spectrometer by spectrometer basis prior to an actual analysis. For this purpose, as described in Patent Literature 1, a conventional mass spectrometer is provided with an auto-tuning function to automatically determine an optimum value of the voltage to be applied to each ion transport optical element, which cancels an analyzer's burden of manually finding the optimum value of the applied voltage. It should be noted that a voltage value as referred to here means an amplitude value of the applied voltage when the applied voltage is a radio-frequency voltage, and means a voltage value itself when the applied voltage is a DC voltage.

When the applied voltage of each ion transport optical element is automatically adjusted using a typical conventional auto-tuning function, the applied voltage is incremented stepwise by a predetermined voltage step within a predetermined voltage range. At each voltage step, the ion intensity of the same component is observed, and a voltage value which maximizes or nearly maximizes the ion intensity is searched for. Normally, when the applied voltage of an ion transport optical element is changed, the ion intensity changes on a bell-shaped curve. Therefore, to find the voltage value which gives the maximum ion intensity, it is necessary to make the increment size (voltage step size) of the applied voltage as small as possible. However, naturally, the smaller the voltage step size is, the larger the number of measurement points becomes, requiring a longer time for automatic adjustment. If, on the other hand, the time for automatic adjustment should be reduced, the voltage step size needs to be increased, in which case the peak of the maximum ion intensity may be missed and the sensitivity is deteriorated.

CITATION LIST

Patent Literature

[Patent Literature 1] JP 2009-192388 A

SUMMARY OF INVENTION

Technical Problem

The present invention has been made to solve the above problem and has an object to provide a mass spectrometer capable of achieving more appropriate voltage adjustment by finding a condition under which ion intensity is maximized or nearly maximized while minimizing the time required to automatically adjust a voltage applied to an ion transport optical element.

Solution to Problem

Through intensive studies, the present inventor has found that change in the ion intensity show a bell-shaped peak as described above when an applied voltage value of an ion transport optical element such as an ion guide is changed, and that the larger the mass-to-charge ratio of the analyzed ion is, the larger the voltage value (absolute value) which gives a maximum ion intensity and the broader the width of the peak become. That is, the larger the mass-to-charge ratio and higher the applied voltage is, the smaller the change in ion intensity per unit amount of voltage change is. When the change in ion intensity per unit amount of voltage change is small, it is possible, even if the voltage is changed at a large step, to find the optimum voltage, i.e. the voltage at which the ion intensity is at its maximum or near it with a smallest intensity drop. Considering this, the present inventor has arrived at the idea of changing a voltage step size according to the applied voltage and mass-to-charge ratio when searching for the optimum voltage by changing the value of applied voltage stepwise.

That is, to solve the above problem, a first invention provides a mass spectrometer equipped with an ion transport optical element between an ion source and a detector, and provided with an adjustment function to optimize a voltage applied to the ion transport optical element based on a result of mass spectrometry of a predetermined component in a sample, comprising:

a) voltage application means for changing the value of voltage applied to the ion transport optical element stepwise at a predetermined step size, and for changing the step size according to the value of voltage; and b) optimum voltage searching means for obtaining ion intensity information on an ion originating from a predetermined component each time the applied voltage is changed by the voltage application means, and for finding a value of voltage which gives a maximum ion intensity based on the ion intensity information.

In the mass spectrometer according to a typical aspect of the first invention, preferably the voltage application means changes the step size continuously or stepwise so as to increase the step size with an increase in the absolute value of the applied voltage.

To solve the above problem, a second invention provides a mass spectrometer equipped with an ion transport optical element between an ion source and a detector, and provided with an adjustment function to optimize a voltage applied to the ion transport optical element based on a result of mass spectrometry of a predetermined component in a sample, comprising:

a) voltage application means for changing the value of voltage applied to the ion transport optical element stepwise at a predetermined step size, and for changing the step size according to a mass-to-charge ratio of an ion to be analyzed; and b) optimum voltage searching means for obtaining ion intensity information on an ion originating from a predetermined component each time the applied voltage is changed by the voltage application means, and for finding a value of voltage which gives a maximum ion intensity based on the ion intensity information.

In the mass spectrometer according to a typical aspect of the second invention, preferably the voltage application means changes the step size continuously or stepwise so as to increase the step size with an increase in the mass-to-charge ratio of the ion to be analyzed.

In the mass spectrometer according to the first invention or second invention, the ion transport optical elements include an ion transport optical element generally known as an ion guide or ion lens, a small-diameter tube adapted to transport ions from an ionization chamber kept at substantially atmospheric pressure to a vacuum chamber in a next stage, a skimmer provided with an ion passage hole and configured to separate vacuum chambers of different pressures, a collision cell, and the like.

Both of the mass spectrometers according to the first invention and the second invention enable checking ion intensity at small voltage intervals within a voltage range in which the change in ion intensity per unit amount of change in the applied voltage is relatively large. Consequently, even if the voltage range which gives a maximum or nearly maximum ion intensity is narrow, a voltage value which gives such a large ion intensity can be spotted precisely without oversight. On the other hand, within a voltage range in which the change in ion intensity per unit amount of change in the applied voltage is relatively small, the ion intensity is checked at coarse voltage intervals. Consequently, even if the voltage range to be searched is large, the number of search points, i.e., measurement points at which ion intensity is obtained can be curbed without overlooking voltage values which give large ion intensities.

Advantageous Effects of Invention

Thus, the mass spectrometers according to the first invention and the second invention steer clear of unnecessary acquisition of ion intensity information in searching for a voltage value that gives a large ion intensity, which makes it possible to reduce the time required to make adjustments to optimize the voltage to be applied to an ion transport optical element. Also, while reducing the time required for adjustments in this way, the mass spectrometers can maintain the accuracy of the adjustments and achieve high analysis sensitivity and analysis accuracy.

DESCRIPTION OF EMBODIMENTS

Figure 1:
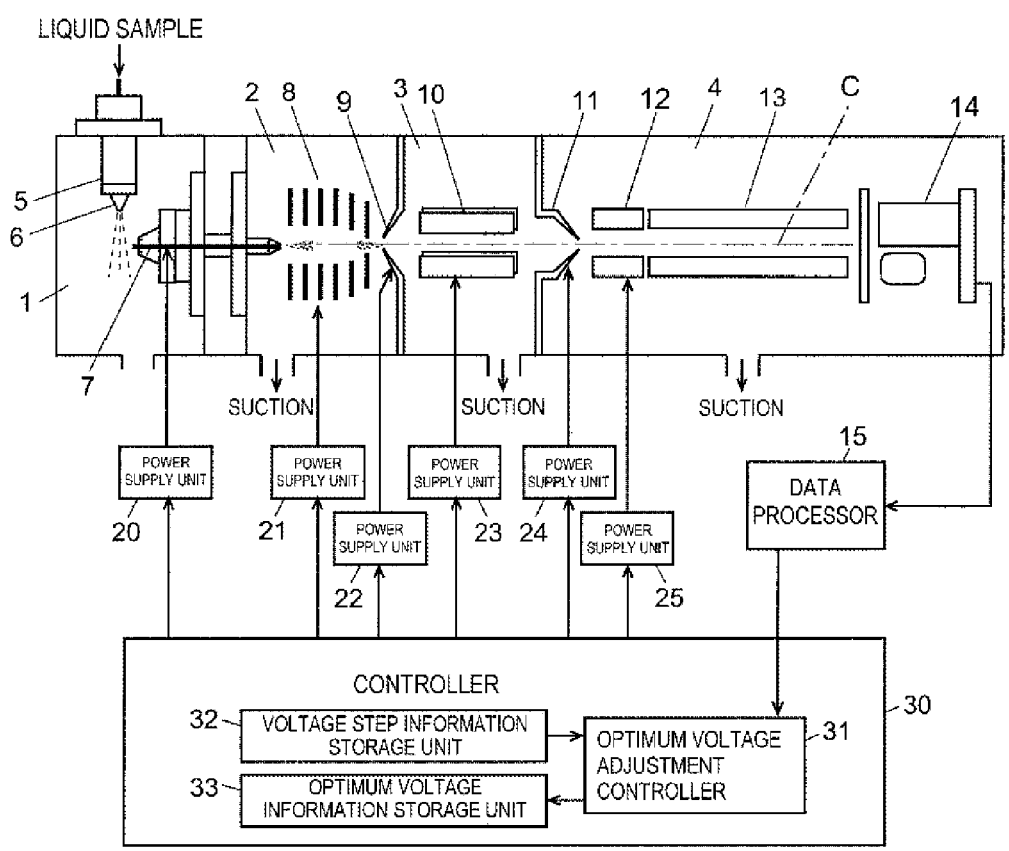
FIG. 1 is a schematic configuration diagram of principal part of a mass spectrometer according to an embodiment of the present invention.

A mass spectrometer according to an embodiment of the present invention is described in detail below with reference to the accompanying drawings. FIG. 1 is a schematic configuration diagram of principal part of a mass spectrometer according to the present embodiment.

The mass spectrometer is an atmospheric pressure ionization mass spectrometer adapted to perform mass spectrometry of various components included in a liquid sample and is configured as a multi-stage differential exhaust system having a first intermediate vacuum chamber 2 and second intermediate vacuum chamber 3 provided between an ionization chamber 1 kept at substantially atmospheric pressure and a high-vacuum analysis chamber 4 exhausted by a high-performance vacuum pump (not shown). The ionization chamber 1 and first intermediate vacuum chamber 2 are communicated via a small-diameter desolvation pipe 7 while the first intermediate vacuum chamber 2 and second intermediate vacuum chamber 3 are communicated through an extremely fine-diameter orifice provided in the top of a skimmer 9.

An ESI ionization probe 5 is disposed in the ionization chamber 1, and a liquid sample containing a sample component or sample components is supplied to the ESI ionization probe 5 as shown in FIG. 1. Upon reaching a nozzle 6 at a tip of the probe 5, the liquid sample is sprayed into the ionization chamber 1 while being given an electric charge. Charged droplets thus sprayed are atomized by colliding with surrounding gas, a solvent in the droplets vaporizes, and the sample component is ionized in the process. Naturally, ionization can also be done using another atmospheric pressure ionization method such as APCI other than ESI. Ions generated in the ionization chamber 1 and fine droplets with the solvent yet to be completely vaporized are drawn into the desolvation pipe 7 by a differential pressure. Then, while the fine droplets pass through the heated desolvation pipe 7, a vaporization of the solvent from the fine droplets further progresses, facilitating ionization.

A first ion guide 8 known as a Q array is installed in the first intermediate vacuum chamber 2, to transport ions by making the ions converge under a relatively high gas pressure. The Q array has a configuration in which four electrode plates are placed in a plane orthogonal to an ion optical axis C, surrounding the ion optical axis C, and plural sets of the four electrode plates are arranged in a direction of the ion optical axis C. The ions fed into the first intermediate vacuum chamber 2 through the desolvation pipe 7 are converged by the first ion guide 8 and enter the second intermediate vacuum chamber 3 through the orifice in the top of the skimmer 9. A second ion guide 10 made up of eight rod electrodes is installed in the second intermediate vacuum chamber 3, the rod electrodes being placed so as to surround the ion optical axis C. While being converged by the second ion guide 10, the ions are fed into the analysis chamber 4 through an opening of an entrance lens electrode 11. A quadrupole mass filter 13 and prefilter 12 are disposed in the analysis chamber 4, where the quadrupole mass filter 13 is made up of four rod electrodes extending in the direction of the ion optical axis C while the prefilter 12 is located in a stage preceding the quadrupole mass filter 13 and made up of four rod electrodes shorter than those of the quadrupole mass filter 13.

Of various types of ions introduced into the analysis chamber 4, only ions having a particular mass-to-charge ratio pass through the quadrupole mass filter 13 and reach an ion detector 14. A detecting signal produced by the ion detector 14 is inputted into a data processor 15 and converted into digital data, and then various types of data processing are performed, including, for example, creation of a mass spectrum, mass chromatogram, and total ion chromatogram.

The desolvation pipe 7, first ion guide 8, skimmer 9, second ion guide 10, entrance lens electrode 11, and prefilter 12 in the mass spectrometer according to the present embodiment are examples of the ion transport optical element according to the present invention. Under the control of a controller 30, a radio-frequency voltage superimposed on a DC voltage, or a DC voltage alone is applied to these elements from respective power supply units 20 to 25. Respective voltages are also applied to the quadrupole mass filter 13, ionization probe 5, and ion detector 14, but description of power supply units used to apply those voltages is omitted here.

The controller 30 includes an optimum voltage adjustment controller 31, a voltage step information storage unit 32, an optimum voltage information storage unit 33, and the like as functional blocks. Operation of these components will be described in detail later. The functions of the data processor 15 and controller 30 can be implemented by a personal computer on which predetermined control/processing software has been installed.

In order for the mass spectrometer according to the present embodiment to achieve high analysis sensitivity and analysis accuracy, it is necessary that the ions to be analyzed out of the ions produced in the ionization chamber 1 (some of the ions are produced in the desolvation pipe 7 or first intermediate vacuum chamber 2) be introduced into the quadrupole mass filter 13 at the highest possible efficiency. For that, it is necessary to maximize or nearly maximize the ion passage efficiency in each of the ion transport optical elements described above. Now, if we note the first ion guide 8, as an example, to maximize the ion passage efficiency of the first ion guide 8, it is important that the voltage value of the radio-frequency voltage and voltage value of a DC bias voltage applied to the first ion guide 8 from the power supply unit 21 are set appropriately according to the mass-to-charge ratios of the ions to be analyzed. For that, the mass spectrometer according to the present embodiment has a characteristic automatic voltage adjustment (auto-tuning) function. Next, operation of the automatic voltage adjustment is described.

Figure 2:
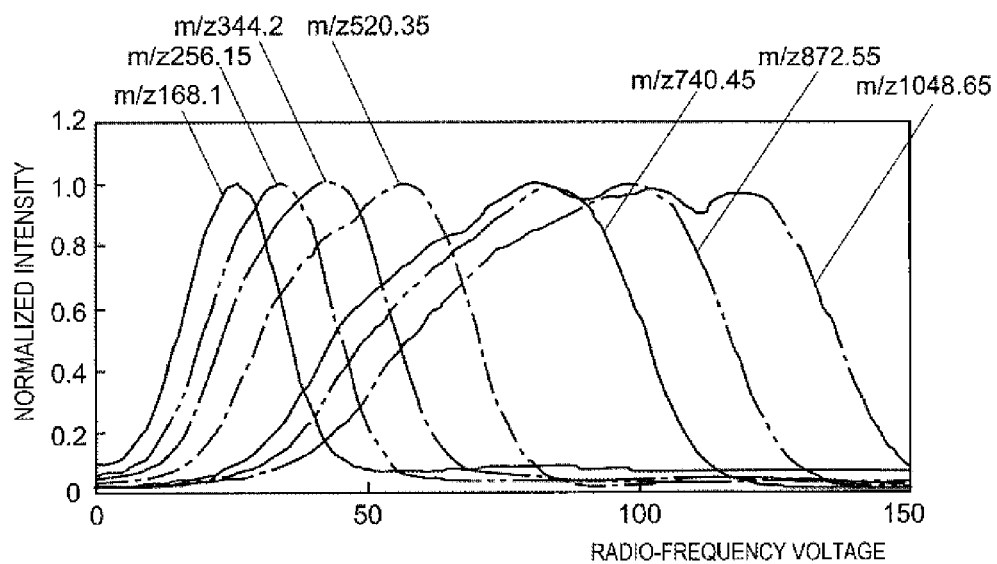
FIG. 2 is a diagram showing actual measurement results of a relationship between a voltage value of a radio-frequency voltage and ion intensity in a Q array.
Figure 3:
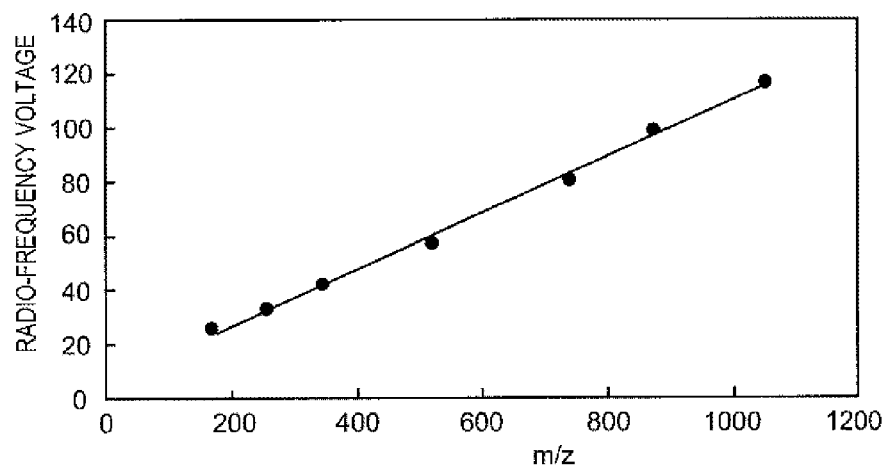
FIG. 3 is a diagram showing a relationship between a mass-to-charge ratio and the voltage value of the radio-frequency voltage based on the actual measurement results of FIG. 2.

FIG. 2 is a diagram showing actual measurement results of a relationship between the voltage value of the radio-frequency voltage applied to the first ion guide 8 and the ion intensity (normalized ion intensity in this embodiment) detected by the ion detector 14, where the measurements have been taken at plural mass-to-charge ratios m/z. In taking the measurements here, the voltage value is changed in 1-volt increments. FIG. 3 is a diagram showing a relationship between the mass-to-charge ratio and an optimum voltage value (voltage value which gives a maximum ion intensity) obtained based on the actual measurement results of FIG. 2. It can be seen from the results in FIG. 2 that the change in the ion intensity with changes in the voltage value of the radio-frequency voltage has an approximately bell-shaped peak, that the larger the mass-to-charge ratio, the higher the optimum voltage value, and that the higher the mass-to-charge ratio, the wider the peak width. Also it can be seen from the results in FIG. 3 that there is a rough proportionality between the mass-to-charge ratio and optimum voltage value.

Specifically, in the case of an ion whose mass-to-charge ratio m/z attains the smallest value of 168.1 among those actually measured, the peak extends within a radio-frequency voltage range of about 10 V to 40 V (with a width of approximately 30 V). On the other hand, in the case of an ion whose mass-to-charge ratio m/z attains the greatest value of 1048.65 among those actually measured, a peak extends within a radio-frequency voltage range of about 50 V to 150 V (with a width of approximately 100 V). The peak shape which represents the change in the ion intensity in relation to the change in the voltage value can be roughly approximated by a Gaussian distribution such as shown in FIG. 4. With a peak which shows such a Gaussian distribution, to spot a peak top appropriately, it is necessary to provide about 20 measurement points within an entire peak range from a start point of the peak to an end point the peak. If this is applied to the peak voltage width found by the above actual measurements, 30V/20=1.5 V is found to be an appropriate voltage step size when m/z=168.1, and 100V/20=5 V is found to be an appropriate voltage step size (hereinafter referred to as an optimum voltage step size) when m/z=1048.65.

Figure 4A:
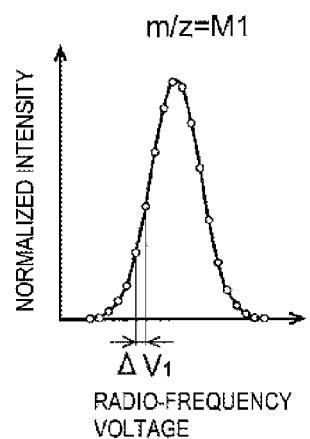
FIG. 4A and FIG. 4B are explanatory diagrams of an automatic voltage adjustment operation in the mass spectrometer according to the present embodiment.
Figure 4B:
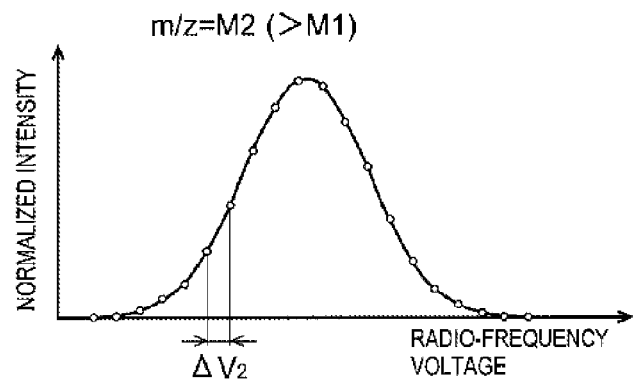

That is, when M1=161.8 in FIG. 4A where the peak width is narrow, the optimum voltage step size $\Delta V_1$ is 1.5 V. On the other hand, when peak width is M2=1048.65 in FIG. 4B where the peak width is relatively wide, the optimum voltage step size $\Delta V_2$ is 5 V. These are optimum voltage step sizes obtained for two given mass-to-charge ratios based on actual measurement results, respectively, and since there is a rough proportionality between the mass-to-charge ratio and optimum voltage value as shown in FIG. 3, the optimum voltage step size at any mass-to-charge ratio can be found by linear interpolation from the optimum voltage step sizes at the above two mass-to-charge ratios. That is, the optimum voltage step size at any mass-to-charge ratio can be found from the straight line indicated by P in FIG. 5.

Figure 5:
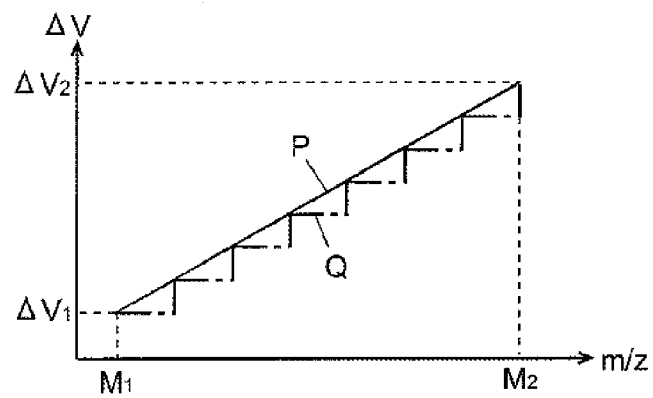
FIG. 5 is an explanatory diagram of an automatic voltage adjustment operation in the mass spectrometer according to the present embodiment.

Thus, in the mass spectrometer according to the present embodiment, a relational expression which represents the straight line P shown in FIG. 5 is stored beforehand in the voltage step information storage unit 32. The relational expression can initially be calculated by the equipment manufacturer based on actual measurement results, but if disassembly and reassembly are performed, for example, to remove contamination of the first ion guide 8 or for other purposes, or if the first ion guide 8 is replaced with a new one, arrangement of electrode plates might change subtly, resulting in a change in the relational expression. To deal with such a situation, a mode for performing measurement and data processing may be provided in order to newly determine the relational expression, and a new relational expression may be obtained when a user gives a command to execute the mode. A table which represents correspondence between the mass-to-charge ratio and optimum voltage step size may be used instead of data which represents a relational expression.

When performing an automatic voltage adjustment for the first ion guide 8, first the optimum voltage adjustment controller 31 finds the optimum voltage step size corresponding to a desired mass-to-charge ratio by referring to a relational expression, such as described above, stored in the voltage step information storage unit 32. For example, if the desired mass-to-charge ratio is M1 in the relational expression shown in FIG. 5, $\Delta V_1$ is found as the optimum voltage step size. Thus, the power supply unit 21 is controlled such that the voltage value of the radio-frequency voltage applied to the first ion guide 8 is changed stepwise in increments of the optimum voltage step size $\Delta V_1$ within a predetermined voltage range. The voltage range through which the voltage is scanned may also be stored in the voltage step information storage unit 32 in correspondence with the mass-to-charge ratio.

Each time the voltage value of the radio-frequency voltage applied to the first ion guide 8 changes, the data processor 15 obtains ion intensity data of an ion originating from a sample component and having a mass-to-charge ratio of M1. The optimum voltage adjustment controller 31 determines magnitude relationship of ion intensities every time one is obtained when the voltage applied to the first ion guide 8 changes, finds the voltage value which maximizes the ion intensity, and stores the voltage value as the optimum voltage value at the mass-to-charge ratio M1 in the optimum voltage information storage unit 33. When optimum voltage values are searched for at plural mass-to-charge ratios, the measurement and processing similar to those described above can be repeated by introducing liquid samples containing sample components corresponding to these mass-to-charge ratios.

If the mass-to-charge ratio to be adjusted is large, the voltage step size becomes larger than when the mass-to-charge ratio is small, but the change in the ion intensity in relation to the change in the voltage value decreases as shown in FIG. 2, making it possible to find a voltage value which gives a maximum or nearly maximum ion intensity even if the voltage step size is large. On the other hand, since the voltage step size increases when the mass-to-charge ratio is large, requiring a smaller number of measurement points at which ion intensity data is obtained, it is possible to reduce the number of measurements and thereby reduce the time required for automatic voltage adjustment.

Regarding the DC voltage applied to the first ion guide 8, using a similar technique, the optimum voltage value can be found by changing the voltage step size according to the targeted mass-to-charge ratio and changing a voltage value stepwise. Similarly, with ion transport optical elements other than the first ion guide 8, the optimum voltage value can be found by changing the voltage step size according to the targeted mass-to-charge ratio and changing the voltage value of the radio-frequency voltage or the voltage value of the DC voltage stepwise. However, depending on the ion transport optical element, the voltage step size has no or negligible dependence on the mass-to-charge ratio. In such a case, there is practically no meaning in changing the voltage step size according to the mass-to-charge ratio, and thus the optimum voltage value can be searched for in increments of a fixed voltage step size regardless of the mass-to-charge ratio as is conventionally the case.

Although in the embodiment described above, the optimum voltage step size is found from the mass-to-charge ratio according to the relational expression represented by the straight line P in FIG. 5, a stepped relationship indicated by the polygonal line Q in FIG. 5 may be converted into data (e.g., into tabular data) and stored in the voltage step information storage unit 32, and then the optimum voltage step size may be calculated from the mass-to-charge ratio based on the stored data. Although linear interpolation is used in the embodiment described above because of a roughly linear relationship between the mass-to-charge ratio and optimum voltage step size, the relationship between the mass-to-charge ratio and optimum voltage step size may be more appropriately approximated by a curve depending on the ion transport optical element. In that case, the relationship between the mass-to-charge ratio and optimum voltage step size can be prescribed by a quadratic or higher-degree expression rather than a linear expression. Also, if it is difficult to define the relationship by an expression, it is apparent that a table or the like can be used.

Next, a mass spectrometer according to another embodiment of the present invention will be described. A configuration of the mass spectrometer according to the present embodiment is basically the same as the above embodiment, and thus description thereof will be omitted. In the above embodiment, noting that the position and spread of the peak change with the mass-to-charge ratio in FIG. 2, control is performed so as to increase the optimum voltage step size when the mass-to-charge ratio is large. Therefore, when an optimum voltage value for a given mass-to-charge ratio is searched for, the voltage step size is constant. That is, in FIG. 4A or FIG. 4B, the voltage step size $\Delta V_1$ or $\Delta V_2$ is constant regardless of the voltage value of the radio-frequency voltage.

On the other hand, when the actual measurement results shown in FIG. 2 are viewed simply in terms of the relationship between the peak width and voltage value, it can be seen that generally, the larger the voltage value (absolute value), the wider the peak width. Thus, based on these actual measurement results, the relationship between the voltage value of the radio-frequency voltage and the optimum voltage step size can be expressed by a linear equation or the like regardless of the mass-to-charge ratio. Specifically, for example, a relationship between any voltage value and optimum voltage step size may be found by linear interpolation from a relationship between an optimum voltage value $V_1$ and the optimum voltage step size $\Delta V_1$ at the mass-to-charge ratio M1 and a relationship between an optimum voltage value $V_2$ and the optimum voltage step size $\Delta V_2$ at the mass-to-charge ratio M2. That is, if the straight line indicated by P' in FIG. 6 is found, the optimum voltage step size for the voltage value of any radio-frequency voltage can be found based on the straight line.

Figure 6:
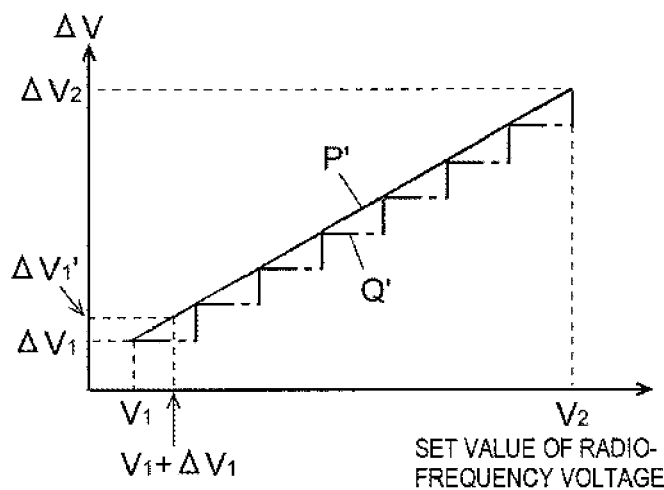
FIG. 6 is an explanatory diagram of an automatic voltage adjustment operation in a mass spectrometer according to another embodiment of the present invention.

Thus, with the mass spectrometer according to the present embodiment, a relational expression of the straight line P' shown in FIG. 6 is stored beforehand in the voltage step information storage unit 32. As with the above embodiment, the relational expression can initially be calculated by the equipment manufacturer based on actual measurement results, but a mode for performing measurement and data processing intended to newly determine the relational expression may be provided such that a new relational expression is obtained when a user gives a command to execute the mode.

When performing an automatic voltage adjustment for the first ion guide 8, the optimum voltage adjustment controller 31 finds the optimum voltage step size corresponding to the value of the radio-frequency voltage to be applied to the first ion guide 8, by referring to a relational expression, such as described above, stored in the voltage step information storage unit 32. In this case, as the voltage value of the applied voltage increases, the optimum voltage step size also increases gradually, and so it is advisable to calculate all the voltage values applied stepwise within a predetermined voltage range, by referring to a relational expression, such as described above, stored in the voltage step information storage unit 32 before the voltage is applied actually.

Specifically, using the relational expression shown in FIG. 6, an optimum voltage step size $\Delta V_1$ is found for the voltage value $V_1$, and for a voltage value $V_1+\Delta V_1$ obtained by increasing the voltage by the step size, $\Delta V_1'$ which is wider than $\Delta V_1$ is found as an optimum voltage step size. All the voltage values to be applied to the first ion guide 8 within a desired voltage range can be found by repeating this process.

As with the above embodiment, an ion intensity is detected each time a value of a voltage applied to the first ion guide 8 is changed, the voltage value which maximizes the ion intensity is found and the voltage value thus found is stored as the optimum voltage value in the optimum voltage information storage unit 33.

Figure 7:
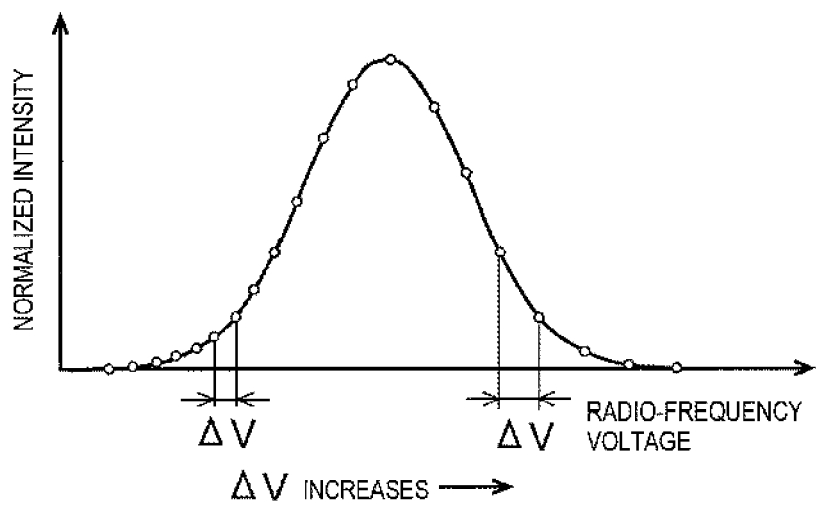
FIG. 7 is an explanatory diagram of an automatic voltage adjustment operation in a mass spectrometer according to another embodiment of the present invention.

FIG. 7 is a diagram showing a relationship between voltage change and ion intensity at a given mass-to-charge ratio during automatic voltage adjustment. As can be seen from FIG. 7, whereas in the above embodiment, the voltage step size is constant when an optimum voltage value for a given mass-to-charge ratio is searched for (see FIG. 4), in the present embodiment, the voltage step size is increased gradually when an optimum voltage value for a given mass-to-charge ratio is searched for. As with the above embodiments, the present embodiment makes it possible to reduce the time required for automatic voltage adjustment without overlooking the optimum voltage value which gives a maximum ion intensity.

As with the above embodiments, the present embodiment allows various modifications. For example, instead of the relational expression represented by the straight line P' in FIG. 6, a stepped relationship indicated by the polygonal line Q' in FIG. 6 may be converted into data, and an optimum voltage step size may be calculated from a voltage value based on the data.

All the embodiments described above are merely examples of the present invention, and thus, naturally any change, modification, or addition made as appropriate to the above description within the spirit and scope of the present invention are included in the scope of the appended claims.

REFERENCE SINGS LIST

1 . . . Ionization Chamber
2 . . . First Intermediate Vacuum Chamber
3 . . . Second Intermediate Vacuum Chamber
4 . . . Analysis Chamber
5 . . . ESI Ionization Probe
6 . . . Nozzle
7 . . . Desolvation Pipe
8 . . . First Ion Guide
9 . . . Skimmer
10 . . . Second Ion Guide
11 . . . Entrance Lens Electrode
12 . . . Prefilter
13 . . . Quadrupole Mass Filter
14 . . . Ion Detector
15 . . . Data Processor
20 to 25 . . . Power Supply Unit
30 . . . Controller
31 . . . Optimum Voltage Adjustment Controller
32 . . . Voltage Step Information Storage Unit
33 . . . Optimum Voltage Information Storage Unit
C . . . Ion Optical Axis

The invention claimed is:

1. A mass spectrometer equipped with an ion transport optical element between an ion source and a detector, and provided with an adjustment function to optimize a voltage applied to the ion transport optical element based on a result of mass spectrometry of a predetermined component in a sample, comprising:
   a) voltage application means for changing a value of voltage applied to the ion transport optical element stepwise at a predetermined step size, and for changing the step size according to the value of voltage; and
   b) optimum voltage searching means for obtaining ion intensity information on an ion originating from a predetermined component each time the applied voltage is changed by the voltage application means, and for finding a value of voltage which gives a maximum ion intensity based on the ion intensity information.

2. The mass spectrometer according to claim 1, wherein the voltage application means changes the step size continuously or stepwise so as to increase the step size with an increase in the absolute value of the applied voltage.

3. A mass spectrometer equipped with an ion transport optical element between an ion source and a detector, and provided with an adjustment function to optimize a voltage applied to the ion transport optical element based on a result of mass spectrometry of a predetermined component in a sample, comprising:
   a) voltage application means for changing a value of voltage applied to the ion transport optical element stepwise at a predetermined step size, and for changing the step size according to a mass-to-charge ratio of an ion to be analyzed; and
   b) optimum voltage searching means for obtaining ion intensity information on an ion originating from a predetermined component each time the applied voltage is changed by the voltage application means, and for finding a value of voltage which gives a maximum ion intensity based on the ion intensity information.

4. The mass spectrometer according to claim 3, wherein the voltage application means changes the step size continuously or stepwise so as to increase the step size with an increase in the mass-to-charge ratio of the ion to be analyzed.

* * * * *